United States Patent
Chung et al.

(10) Patent No.: US 9,637,519 B2
(45) Date of Patent: May 2, 2017

(54) PEPTIDE FOR INDUCING MAST CELL-SPECIFIC APOPTOSIS AND USE THEREOF

(71) Applicant: CAREGEN CO., LTD., Anyang-si (KR)

(72) Inventors: Young Ji Chung, Yongin-si (KR); Eun Mi Kim, Gunpo-si (KR); Eung-Ji Lee, Anyang-si (KR); Tae-Hoon Lee, Sangju-si (KR); Young-Min Lee, Siheung-si (KR)

(73) Assignee: CAREGEN CO., LTD., Anyang-si (KR)

( * ) Notice: Subject to any disclaimer, the term of this patent is extended or adjusted under 35 U.S.C. 154(b) by 0 days.

(21) Appl. No.: 14/888,017

(22) PCT Filed: Oct. 25, 2013

(86) PCT No.: PCT/KR2013/009601
§ 371 (c)(1),
(2) Date: Oct. 29, 2015

(87) PCT Pub. No.: WO2014/185604
PCT Pub. Date: Nov. 20, 2014

(65) Prior Publication Data
US 2016/0075739 A1 Mar. 17, 2016

(30) Foreign Application Priority Data
May 13, 2013 (KR) .................. 10-2013-0053779

(51) Int. Cl.
*A61K 38/00* (2006.01)
*A61K 38/10* (2006.01)
*C07K 7/08* (2006.01)
*C07K 14/705* (2006.01)
*G01N 33/50* (2006.01)

(52) U.S. Cl.
CPC .......... *C07K 7/08* (2013.01); *C07K 14/70521* (2013.01); *G01N 33/5023* (2013.01); *A61K 38/00* (2013.01); *G01N 2333/4703* (2013.01); *G01N 2333/70535* (2013.01); *G01N 2500/02* (2013.01); *G01N 2500/10* (2013.01)

(58) Field of Classification Search
CPC .. A61K 38/00; A61K 38/10; C07K 14/70521; C07K 7/08
USPC ........ 514/16.4, 18.7, 1.6, 1.7, 1.9, 21.5, 4.8, 514/6.9, 7.4; 530/327
See application file for complete search history.

(56) References Cited

U.S. PATENT DOCUMENTS 8,436,137 B2 * 5/2013 Kawakami ....... A61K 47/48276
435/252.3

OTHER PUBLICATIONS

G1MYR4 from UniProt, pp. 1-6. Last sequence update Oct. 19, 2011.*
Steinman et al, "How to successfully apply animal studies in experimental allergic encephalomyelitis to research on multiple sclerosis," Ann. Neurol., 2006, 60: 12-21.*
Siriam et al, "Experimental allergic encephalomyelitis: A misleading model of Multiple Sclerosis," Ann. Neurol., 2005, 58: 939-945.*
Rehumatoid Arthritis from Merck Manual, pp. 1-18. Accessed Apr. 21, 2016.*

* cited by examiner

*Primary Examiner* — Julie Ha
(74) *Attorney, Agent, or Firm* — Clark & Elbing LLP; Susan M. Michaud

(57) ABSTRACT

A peptide according to the present invention can perform a function identical or similar to the function of natural CTLA-4 and has an excellent degree of skin penetration due to a small size. The peptide according to the present invention effectively binds to antigen presenting cell surface proteins (CD80 and CD86) to inhibit activity of T cells and thus is capable of inhibiting the expression of inflammatory cytokines (for example, IL-2 and IFN-γ). As a result, a composition comprising the peptide according to the present invention exhibits excellent effects in terms of preventing, treating, or improving Th1-mediated immune diseases. Therefore, the superior activity and stability of the peptide according to the present invention can be useful when applied to medicine, quasi-drugs, and cosmetics.

14 Claims, 5 Drawing Sheets

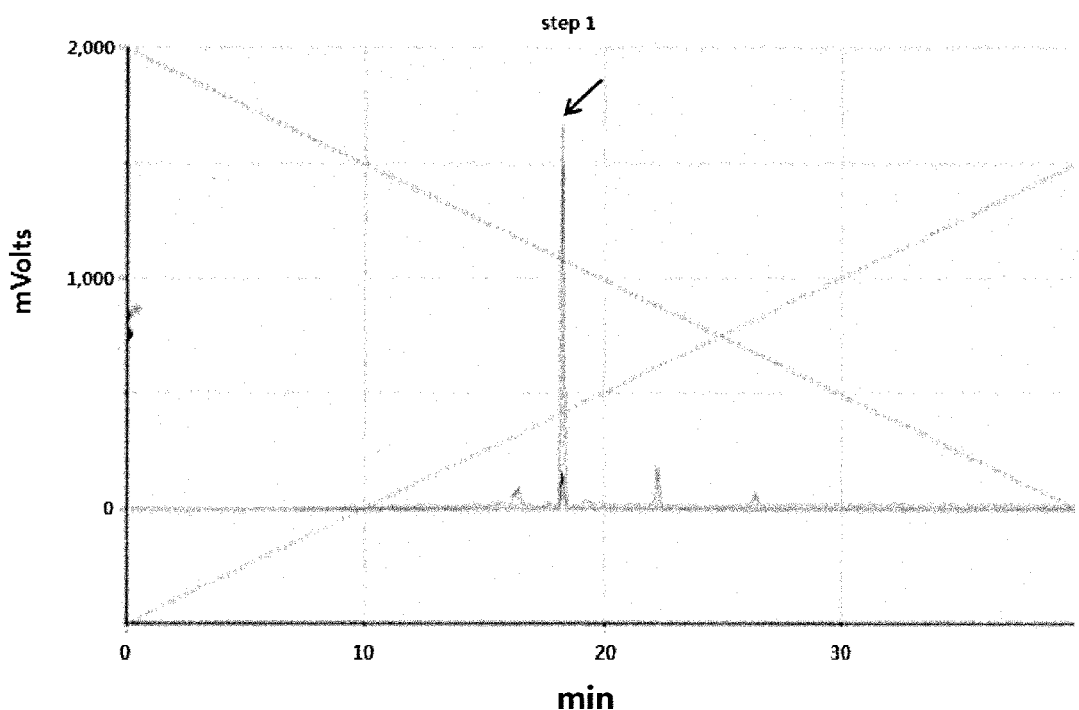
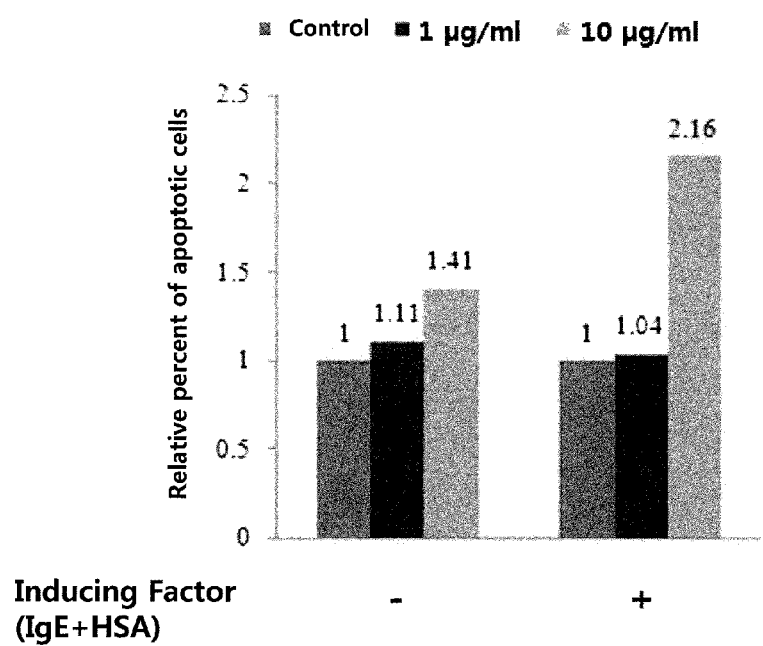

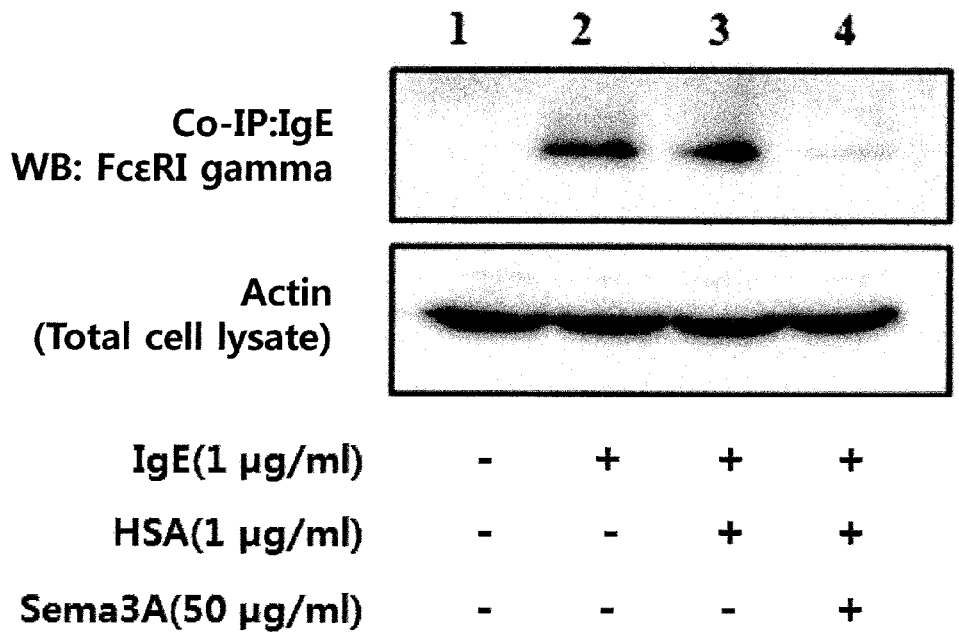
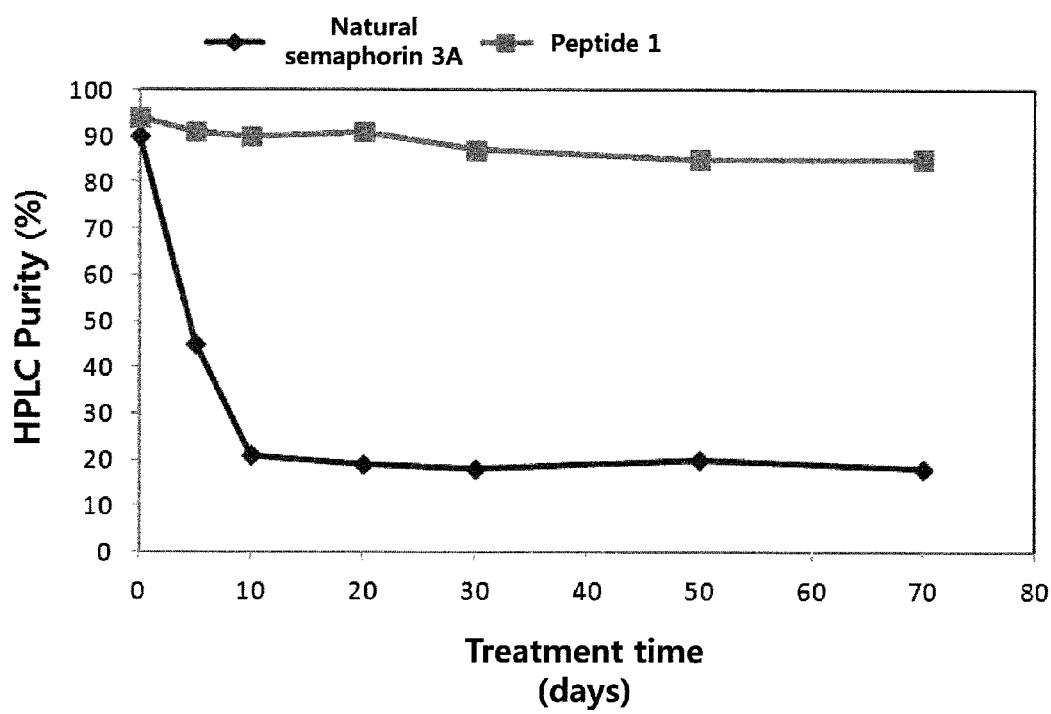

SEQUENCE LISTING

<160> NUMBER OF SEQ ID NOS: 2

<210> SEQ ID NO 1

```
<211> LENGTH: 12
<212> TYPE: PRT
<213> ORGANISM: Artificial Sequence
<220> FEATURE:
<223> OTHER INFORMATION: Sema3A peptide 1

<400> SEQUENCE: 1

Trp Val Pro Tyr Gln Ala Arg Val Pro Tyr Pro Arg
1               5                   10

<210> SEQ ID NO 2
<211> LENGTH: 771
<212> TYPE: PRT
<213> ORGANISM: Homo sapiens

<400> SEQUENCE: 2

Met Gly Trp Leu Thr Arg Ile Val Cys Leu Phe Trp Gly Val Leu Leu
1               5                   10                  15

Thr Ala Arg Ala Asn Tyr Gln Asn Gly Lys Asn Asn Val Pro Arg Leu
            20                  25                  30

Lys Leu Ser Tyr Lys Glu Met Leu Glu Ser Asn Asn Val Ile Thr Phe
        35                  40                  45

Asn Gly Leu Ala Asn Ser Ser Tyr His Thr Phe Leu Leu Asp Glu
    50                  55                  60

Glu Arg Ser Arg Leu Tyr Val Gly Ala Lys Asp His Ile Phe Ser Phe
65                  70                  75                  80

Asp Leu Val Asn Ile Lys Asp Phe Gln Lys Ile Val Trp Pro Val Ser
                85                  90                  95

Tyr Thr Arg Arg Asp Glu Cys Lys Trp Ala Gly Lys Asp Ile Leu Lys
            100                 105                 110

Glu Cys Ala Asn Phe Ile Lys Val Leu Lys Ala Tyr Asn Gln Thr His
        115                 120                 125

Leu Tyr Ala Cys Gly Thr Gly Ala Phe His Pro Ile Cys Thr Tyr Ile
    130                 135                 140

Glu Ile Gly His His Pro Glu Asp Asn Ile Phe Lys Leu Glu Asn Ser
145                 150                 155                 160

His Phe Glu Asn Gly Arg Gly Lys Ser Pro Tyr Asp Pro Lys Leu Leu
                165                 170                 175

Thr Ala Ser Leu Leu Ile Asp Gly Glu Leu Tyr Ser Gly Thr Ala Ala
            180                 185                 190

Asp Phe Met Gly Arg Asp Phe Ala Ile Phe Arg Thr Leu Gly His His
        195                 200                 205

His Pro Ile Arg Thr Glu Gln His Asp Ser Arg Trp Leu Asn Asp Pro
    210                 215                 220

Lys Phe Ile Ser Ala His Leu Ile Ser Glu Ser Asp Asn Pro Glu Asp
225                 230                 235                 240

Asp Lys Val Tyr Phe Phe Phe Arg Glu Asn Ala Ile Asp Gly Glu His
                245                 250                 255

Ser Gly Lys Ala Thr His Ala Arg Ile Gly Gln Ile Cys Lys Asn Asp
            260                 265                 270

Phe Gly Gly His Arg Ser Leu Val Asn Lys Trp Thr Thr Phe Leu Lys
        275                 280                 285

Ala Arg Leu Ile Cys Ser Val Pro Gly Pro Asn Gly Ile Asp Thr His
    290                 295                 300

Phe Asp Glu Leu Gln Asp Val Phe Leu Met Asn Phe Lys Asp Pro Lys
305                 310                 315                 320
```

```
Asn Pro Val Val Tyr Gly Val Phe Thr Thr Ser Ser Asn Ile Phe Lys
                325                 330                 335

Gly Ser Ala Val Cys Met Tyr Ser Met Ser Asp Val Arg Arg Val Phe
            340                 345                 350

Leu Gly Pro Tyr Ala His Arg Asp Gly Pro Asn Tyr Gln Trp Val Pro
        355                 360                 365

Tyr Gln Gly Arg Val Pro Tyr Pro Arg Pro Gly Thr Cys Pro Ser Lys
370                 375                 380

Thr Phe Gly Gly Phe Asp Ser Thr Lys Asp Leu Pro Asp Val Ile
385                 390                 395                 400

Thr Phe Ala Arg Ser His Pro Ala Met Tyr Asn Pro Val Phe Pro Met
                405                 410                 415

Asn Asn Arg Pro Ile Val Ile Lys Thr Asp Val Asn Tyr Gln Phe Thr
            420                 425                 430

Gln Ile Val Val Asp Arg Val Asp Ala Glu Asp Gly Gln Tyr Asp Val
        435                 440                 445

Met Phe Ile Gly Thr Asp Val Gly Thr Val Leu Lys Val Ser Ile
    450                 455                 460

Pro Lys Glu Thr Trp Tyr Asp Leu Glu Glu Val Leu Leu Glu Met
465                 470                 475                 480

Thr Val Phe Arg Glu Pro Thr Ala Ile Ser Ala Met Glu Leu Ser Thr
                485                 490                 495

Lys Gln Gln Gln Leu Tyr Ile Gly Ser Thr Ala Gly Val Ala Gln Leu
            500                 505                 510

Pro Leu His Arg Cys Asp Ile Tyr Gly Lys Ala Cys Glu Cys Cys
        515                 520                 525

Leu Ala Arg Asp Pro Tyr Cys Ala Trp Asp Gly Ser Ala Cys Ser Arg
530                 535                 540

Tyr Phe Pro Thr Ala Lys Arg Thr Arg Arg Gln Asp Ile Arg Asn
545                 550                 555                 560

Gly Asp Pro Leu Thr His Cys Ser Asp Leu His His Asp Asn His His
            565                 570                 575

Gly His Ser Pro Glu Glu Arg Ile Ile Tyr Gly Val Glu Asn Ser Ser
        580                 585                 590

Thr Phe Leu Glu Cys Ser Pro Lys Ser Gln Arg Ala Leu Val Tyr Trp
            595                 600                 605

Gln Phe Gln Arg Arg Asn Glu Glu Arg Lys Glu Glu Ile Arg Val Asp
        610                 615                 620

Asp His Ile Ile Arg Thr Asp Gln Gly Leu Leu Leu Arg Ser Leu Gln
625                 630                 635                 640

Gln Lys Asp Ser Gly Asn Tyr Leu Cys His Ala Val Glu His Gly Phe
            645                 650                 655

Ile Gln Thr Leu Leu Lys Val Thr Leu Glu Val Ile Asp Thr Glu His
        660                 665                 670

Leu Glu Glu Leu Leu His Lys Asp Asp Gly Asp Gly Ser Lys Thr
    675                 680                 685

Lys Glu Met Ser Asn Ser Met Thr Pro Ser Gln Lys Val Trp Tyr Arg
690                 695                 700

Asp Phe Met Gln Leu Ile Asn His Pro Asn Leu Asn Thr Met Asp Glu
705                 710                 715                 720

Phe Cys Glu Gln Val Trp Lys Arg Asp Arg Lys Gln Arg Arg Gln Arg
                725                 730                 735

Pro Gly His Thr Pro Gly Asn Ser Asn Lys Trp Lys His Leu Gln Glu
```

```
                    740                 745                 750
Asn Lys Lys Gly Arg Asn Arg Arg Thr His Glu Phe Glu Arg Ala Pro
            755                 760                 765

Arg Ser Val
    770
```

PEPTIDE FOR INDUCING MAST CELL-SPECIFIC APOPTOSIS AND USE THEREOF

TECHNICAL FIELD

The present patent application claims priority to and the benefit of Korean Patent Application No. 10-2013-0053779 filed in the Korean Intellectual Property Office on 13 May 2013, the entire contents of which are incorporated herein by reference.

The present invention relates to a peptide for inducing mast cell-specific apoptosis and a use thereof.

BACKGROUND ART

Hypersensitivity reactions generally known as allergies are called abnormal immune responses against antigens. These reactions are classified into four main types according to the Gell & Coombs classification: type I hypersensitivity reaction mediated by IgE, type II hypersensitivity reaction mediated by antibodies, type III hypersensitivity reaction mediated by immune complexes, and type IV hypersensitivity reaction mediated by interactions between antigen presenting cells and T cells. Allergic diseases commonly found in the surroundings are mostly caused by type I hypersensitivity reaction, and include allergic rhinitis, asthma, allergic dermatitis, and the like. There are foods, such as nuts and eggs, pollen, dust mites, and some drugs which are well known allergens (antigens). These allergens are combined with IgE, attached to $\alpha$-subunits of FI$\epsilon$RI, which is a IgE receptor of mast cells, and forms complexes together with $\beta$ and $\gamma$-subunits, thereby enabling signaling of the receptors. Through this procedure, the degranulation of mast cells is induced to activate the secretion of histamine, beta-hexosaminidase, prostaglandin, leukotriene, interleukin (IL)-4, IL-5, IL-6, and TNF-$\alpha$, which are factors that causes itching or inflammation responses. The actions of these factors may be aggravating factors of allergic reactions by activating IgE production of B cells. It has been known that high serum IgE levels are actually observed in allergic patients, and thus the inflow of allergens easily causes hypersensitivity reactions (Allergy Asthma Immunol Res., 5(3): 170-174(2013)).

Diseases are classified according to the area in which type I hypersensitivity reaction is observed. The hypersensitivity reaction results in allergic rhinitis in the nasal mucosa, asthma in the airway mucosa or bronchial tubes, and atopic dermatitis in the skin.

The atopic dermatitis prevalence rate in people over 1 year old people was 6.1% according to the National Health and Nutrition Examination Survey results (National Health and Nutrition Examination Survey, the Ministry of Health and Welfare) reported in 2010, and the atopic dermatitis prevalence rate of 13-18 year old adolescents was 23.1% in the 2011 Youth Health Behavior Online Survey (Youth health behavior online survey, the Ministry of Health and Welfare). Lesions begin due to general allergens or IgE stimulation, and patients scratch the affected parts because of itching caused by the stimulation of histamine secreted from degranulation of mast cells, resulting in, secondarily, the inflow of *Staphylococcus aureus, S. epidermidis*, and the like, which are skin flora. It is known that the inflow of such foreign antigens may cause additional inflammation responses in the affected parts or worsen diseases (Allergy Asthma Proc., May-June; 33(2012)).

Therapeutic agents for atopic dermatitis include steroids showing anti-inflammatory actions through immunosuppressive effects, antihistamines blocking the release of histamine from mast cells, antibiotics, and the like. However, the steroid use for a long period of time causes side effects, such as hair growing, skin thinning, and bacterial infection, and the steroid withdrawal causes rapid aggravation of symptoms. It has been reported that the antihistamine use for a long period of time causes side effects, such as insomnia, anxiety, and loss of appetite. The antibiotic use for a long period of time also causes side effects, such as antibiotic resistance. Therefore, the development of more effective therapeutic agents capable of minimizing side effects is required.

In vivo proteins can minimize side effects due to high biocompatibility thereof. However, proteins per se have too low stability and high production costs for the use as therapeutic agents. Peptide preparations that use particular effective regions of the in vivo proteins have the same efficacies and can solve problems in association with stability and production costs. Therefore, the present researchers conducted research that utilizes anti-allergic effects of peptides derived from in vivo proteins, capable of suppressing the activation of mast cells.

Semaphorin 3A is one of semaphorin proteins that have a common cysteine-rich domain called a Sema domain. Semaphorin protein was first known as a repulsive axon guidance factor in the nervous system development process. Class 3 semaphorins are secreted proteins, include six kinds ranging from Sema3A to Sema3F, and deliver signals by forming receptor complexes together with Plexin A receptor and Neurophilin receptor. As known in the early stages, semaphorin 3A guides the contraction of nerve growth factor (NGF)-sensitive neurons or is expressed from activated T cells and dendritic cells, thereby regulating T cell growth or cytokine secretion.

Throughout this application, various patents and publications are referenced and citations are provided in parentheses. The disclosure of these patents and publications in their entities are hereby incorporated by references into this application in order to more fully describe this invention and the state of the art to which this invention pertains.

DETAILED DESCRIPTION OF THE INVENTION

Technical Problem

The present inventors have endeavored to develop a material which has excellent activity and stability compared with the natural semaphorin 3A protein while retaining the same or similar functions to semaphorin 3A. As a result, the present inventors have selected a semaphorin 3A-derived peptide having excellent bioactivity (e.g., inducing mast cell-specific apoptosis, suppressing mast cell activity, inhibiting Fc$\epsilon$RI protein signaling, etc.) among many peptide candidates, and then have completed the present invention.

Therefore, an aspect of the present invention is to provide a peptide composed of SEQ ID NO: 1.

Another aspect of the present invention is to provide a pharmaceutical composition for preventing or treating Th2-mediated immune diseases.

Another aspect of the present invention is to provide a pharmaceutical composition for preventing or treating autoimmune diseases.

Another aspect of the present invention is to provide a pharmaceutical composition for preventing or treating mast cell-induced inflammation diseases.

Still another aspect of the present invention is to provide a method for screening a mast cell-induced disease therapeutic agent.

Still another aspect of the present invention is to provide a method for preventing or treating Th2-mediated immune diseases.

Still another aspect of the present invention is to provide a method for preventing or treating autoimmune diseases.

Still another aspect of the present invention is to provide a method for preventing or treating mast cell-induced inflammation diseases.

Other purposes and advantages of the present disclosure will become more obvious with the following detailed description of the invention, claims, and drawings.

Technical Solution

In accordance with an aspect of the present invention, there is provided a peptide composed of an amino acid sequence of SEQ ID NO: 1.

The present inventors have endeavored to develop a material which has excellent activity and stability compared with the natural semaphorin A protein while retaining the same or similar functions to semaphorin 3A. As a result, the present inventors have selected a semaphorin 3A-derived peptide having excellent bioactivity (e.g., inducing mast cell-specific apoptosis, suppressing mast cell activity, inhibiting FcεRI protein signaling, etc.) among many peptide candidates.

Semaphorins are a large protein family that includes secreted and membrane-binding proteins, and are characterized by an extracellular domain containing a semaphorin domain composed of 500 amino acid residues. Of these, semaphorin 3A is a secreted protein which belongs to the class 3 semaphorin family, and is known to perform various intracellular functions, such as regulating development procedures including cell migration, morphogenesis, and tissue remodeling, by mediating cell-repelling cues through neuropilins and plexins (PLXNs) receptors, as well as the guidance of neuronal axons. Structurally, the Sema domain present in the semaphorin is important in functioning as a protein interaction module during the axon guidance procedure. The Sema domain is also present in liver cell growth factor receptors, sexual proteins, and viral proteins. The Sema domain is characterized by a highly conserved set of cysteine residues, which form four disulfide bonds to structurally stabilize proteins.

Meanwhile, it has been reported that the knockout of the semaphorin 3A gene induces abnormal bone and cartilage development, and the semaphorin 3A-related signaling molecules (Semaphorin 3A, Neuropilin-1, and plexins PLXNA1 and PLXNA2) are expressed in the endochondral ossification. This means latent roles thereof in the skeletal development and neural distribution.

The present inventors synthesized a plurality of semaphorin 3A-derived peptides which exhibit the above-described characteristics, based on moieties associated with functions of human semaphorin 3A. More specifically, the present inventors selectively prepared peptides of the present invention by arbitrarily partially synthesizing several moieties of the semaphorin 3A protein to first search for moieties which can bind to receptor proteins, and then optimizing the amino acid sequences of the predicted moieties. Of these candidate peptides, a peptide having the most excellent activity was screened, and thus the peptide of SEQ ID NO: 1 of the present invention was prepared.

According to a certain embodiment of the present invention, the peptide of SEQ ID NO: 1 of the present invention is derived from human semaphorin 3A (GenBank Accession Number, NP_006071; SEQ ID NO: 2), and shown in table 1.

The peptide of the present invention has functions of natural human semaphorin 3A (e.g., anti-allergic activity), and effectively showed the induction of mast cell-specific apoptosis and the inhibition of mast cell activity (see FIGS. 2a-2c and FIGS. 3a-3b). In addition, the peptide of the present invention suppressed the complex formation of the FcεRI receptor (see FIGS. 4a-4c).

According to a certain embodiment of the present invention, the peptide of the present invention induces mast cell-specific apoptosis.

According to a certain embodiment of the present invention, the peptide of the present invention reduces the amount of histamine secreted by mast cells, and inhibits the intercellular activity of beta-hexosaminidase.

According to a certain embodiment of the present invention, the peptide of the present invention inhibits FcεRI signaling. The FcεRI signaling is inhibited by suppressing the complex formation of the FcεRI receptor, and inhibiting the complex formation of the FcεRI receptor may be verified through the inhibition of ERK1/2, p38, or Lyn phosphorylation.

The term used herein "peptide" refers to a linear molecule formed by linking between amino acid residues through peptide bonds. The peptides of the present invention may be prepared by conventional chemical synthesis processes known to one of skill in the art, in particular, solid-phase synthesis techniques (Merrifield, *J. Amer. Chem. Soc.* 85: 2149-54 (1963); Stewart, et al., *Solid Phase Peptide Synthesis,* 2nd. ed., Pierce Chem. Co.: Rockford, 111 (1984)).

The peptide of the present invention per se has excellent stability compared with the natural semaphorin 3A protein, but the stability thereof can be further improved through amino acid modification.

According to the present invention, the peptide of the present invention has very excellent thermal stability compared with the natural semaphorin 3A protein. The natural semaphorin 3A protein has low stability at the time of storage for a long period of time as well as difficulty in the preparation and high production costs. However, the peptide of the present invention can be mass-produced at a very low cost, and can maximally prevent the deterioration in bioactivity due to physical and chemical stability at high temperatures, and has further improved therapeutic effects by increasing the remaining period in vivo (see FIG. 5). Therefore, the peptide of the present invention can be favorably applied to product requiring long-term storage, such as medicines, quasi-medicines, and cosmetics.

According to a certain embodiment of the present invention, the N-terminal or C-terminal of the peptide may be modified into a hydroxyl group (—OH), an amino group (—NH$_2$), an azide group (—NHNH$_2$), or the like.

According to a preferable embodiment, the peptides of this invention have at their N-terminal a protection group selected from the group consisting of acetyl group, fluorenyl methoxy carbonyl group, formyl group, palmitoyl group, myristyl group, stearyl group and polyethylene glycol (PEG).

The modifications of peptides described above greatly increase the stability of the peptides of this invention. The term used herein "stability" refers to in vivo stability and storage stability (e.g., storage stability at room temperature) as well. The protection group described above protects the peptides from the attack of protease in vivo.

In accordance with another aspect of the present invention, there is provided a pharmaceutical composition for preventing or treating Th2-mediated immune diseases, containing the foregoing peptide as an active ingredient.

In accordance with still another aspect of the present invention, there is provided a pharmaceutical composition for preventing or treating autoimmune diseases, containing the foregoing peptide as an active ingredient.

Since the present composition comprises the Semaphorin 3A-derived peptides of this invention as active ingredients described above, the common descriptions between them are omitted in order to avoid undue redundancy leading to the complexity of this specification.

According to a certain embodiment of the present invention, the Th2-mediated immune diseases of the present invention include, but are not limited to, allergic rhinitis, bronchial asthma, atopic dermatitis, contact dermatitis, allergic conjunctivitis, urticaria, vascular edema, food allergy, physical allergy, hypersensitive pneumonitis, occupational allergic diseases, and drug allergy.

According to a certain embodiment of the present invention, the autoimmune diseases of the present invention are caused through the activation of the Lyn kinase-mediated pathway, and the activation of the Lyn kinase-mediated pathway is triggered through an increase in the phosphorylation of Lyn kinase.

According to a certain embodiment of the present invention, the autoimmune diseases of the present invention include, but are not limited to, obesity, hyperlipidemia, diabetes, atherosclerosis, and metabolic syndrome.

In accordance with still another aspect of the present invention, there is provided a pharmaceutical composition for preventing or treating mast cell-induced inflammatory diseases, containing the foregoing peptide as an active ingredient.

Since the present composition comprises the Semaphorin 3A-derived peptides of this invention as active ingredients described above, the common descriptions between them are omitted in order to avoid undue redundancy leading to the complexity of this specification.

According to a certain embodiment of the present invention, the pharmaceutical composition of the present invention induces mast cell-specific apoptosis.

According to a certain embodiment of the present invention, the mast cell-induced inflammatory diseases include, but are not limited to, asthma, atopic dermatitis, psoriasis, interstitial cystitis, obesity, multiple sclerosis, coronary artery disease (CAD), arthritis, and inflammatory bowel disease (IBD).

According to a preferable embodiment, the composition is a pharmaceutical composition containing: (a) a pharmaceutically effective amount of the peptide having Semaphorin 3A protein activity of the present invention; and (b) a pharmaceutically acceptable carrier.

The term used herein "pharmaceutically effective amount" refers to an amount enough to show and accomplish efficacies and activities of the Semaphorin 3A protein-related peptide of this invention.

The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition of the present disclosure may further include, in addition to above-described components, a lubricant, a wetting agent, a sweetener, a fragrance, an emulsifier, a suspending agent, a preservative, or the like. Suitable pharmaceutically acceptable carriers and formulations are described in detail in Remington's Pharmaceutical Sciences (19th ed., 1995).

The pharmaceutical composition of the present disclosure may be administered orally or parenterally. For parenteral administration, it may be administered intravenously, subcutaneously, intramuscularly, intraabdominally, transdermally, or the like.

An appropriate dosage of the pharmaceutical composition of the present disclosure may be determined variously depending on such factors as preparation method, administration method, age, body weight and sex of the patient, pathological condition, diet, administration time, administration route, excretion rate or response sensitivity. A recommended dosage of the pharmaceutical composition of the present disclosure is 0.0005-1,000 mg/kg per day.

The pharmaceutical composition of the present disclosure may be prepared into a unit dosage form or multiple dosage form along with a pharmaceutically acceptable carrier and/or excipient according to a method that can be easily employed by those skilled in the art. The formulation may be in the form of solution in oily or aqueous medium, suspension, emulsion, extract, powder, granule, tablet, capsule or gel (e.g., hydrogel), and may further include a dispersant or stabilizer.

The composition of the present disclosure is a cosmetic composition comprising: (a) a cosmetically effective amount of the Semaphorin 3A-related peptide of the present disclosure described above; and (b) a pharmaceutically acceptable carrier.

As used herein, the term "cosmetically effective amount" refers to an amount sufficient of the composition of the present disclosure to achieve cosmetic efficacies of the present composition.

The cosmetic composition of the present disclosure may be formulated into any form commonly used in the art. Non-limiting examples include solution, suspension, emulsion, paste, gel, cream, lotion, powder, soap, surfactant-containing cleanser, oil, powder foundation, emulsion foundation, wax foundation, spray, etc. More specifically, it may be prepared into soothing lotion, nourishing lotion, nourishing cream, massage cream, essence, eye cream, cleansing cream, cleansing foam, cleansing water, pack, spray or powder.

When the composition of the present disclosure is in the form of paste, cream or gel, animal oil, plant oil, wax, paraffin, starch, tragacanth, cellulose derivatives, polyethylene glycol, silicone, bentonite, silica, talc, zinc oxide, etc. may be used as the carrier.

When the composition of the present disclosure is in the form of powder or spray, lactose, talc, silica, aluminum hydroxide, calcium silicate or polyamide powder may be used as the carrier. Especially, the spray may further comprise a propellant such as hydrochlorofluorocarbon, propane/butane or dimethyl ether.

When the composition of the present disclosure is in the form of solution or emulsion, a solvent, solubilizer or emulsifier may be used as the carrier, examples of which include water, ethanol, isopropanol, ethyl carbonate, ethyl acetate, benzyl alcohol, benzyl benzoate, propylene glycol, 1,3-butylglycol oil, glycerol aliphatic ester, polyethylene glycol, or sorbitan fatty acid ester.

When the composition of the present disclosure is in the form of suspension, a liquid diluent such as water, ethanol or propylene glycol, a suspension such as ethoxylated isostearyl alcohol, polyoxyethylene sorbitol ester and polyoxyethylene sorbitan ester, microcrystalline cellulose, aluminum metahydroxide, bentonite, agar, tragacanth, etc. may be used as the carrier.

When the composition of the present disclosure is in the form of surfactant-containing cleanser, aliphatic alcohol sulfate, aliphatic alcohol ether sulfate, sulfosuccinic acid monoester, isethionate, imidazolinium derivatives, methyl taurate, sarcosinate, fatty acid amide ether sulfate, alkylamidobetaine, aliphatic alcohol, fatty acid glyceride, fatty acid diethanolamide, vegetable oil, lanolin derivatives, ethoxylated glycerol fatty acid ester, etc. may be used as the carrier.

In addition to the peptide as the active ingredient and the carrier ingredients, the cosmetic composition of the present disclosure may further comprise those ingredients commonly used in cosmetic compositions. Examples include common adjuvants such as antioxidant, stabilizer, solubilizer, vitamin, pigment and fragrance.

In accordance with still another aspect of the present invention, there is provided a method for screening a mast cell-induced inflammatory disease therapeutic agent, the method including: (a) treating cells containing a semaphorin 3A-encoding nucleotide sequence with a test material; and (b) analyzing the expression or activity of the intracellular semaphorin 3A protein, wherein the test material is determined as a mast cell-induced inflammatory disease therapeutic agent if the test material suppresses the complex formation of FcεRI receptor by overexpressing the semaphorin 3A protein or increasing activity of the semaphorin 3A protein.

Since the method of the present invention entails semaphorin 3A protein containing the foregoing semaphorin 3A-derived peptide of the present invention, descriptions of overlapping contents between the two are omitted to avoid excessive complexity of the specification due to repetitive descriptions thereof.

According to the method of the present invention, first, cells containing a semaphorin 3A-encoding nucleotide sequence are contacted with a test material to be analyzed. The cells containing the nucleotide sequence of the target of the present invention are not particularly limited, but mast cells are preferably excluded since the overexpression of the semaphorin 3A protein may induce the apoptosis of mast cells. As used herein to recite the screening method of the present invention, the term "test material" refers to an unknown material which is used in screening to test whether or not the test material influences the activity of the semaphorin 3A gene or protein or whether or not the test material inhibits the complex formation of the FcεRI receptor by the semaphorin 3A protein. The test material includes, but is not limited to, chemical materials, peptides, and natural extracts. The test material analyzed by the screening method of the present invention is a single compound, a mixture of compounds (e.g., a natural extract or a cell or tissue culture), an antibody, or a peptide. The test material may be obtained from synthetic or natural compound libraries. These compound libraries are obtained by methods known in the art. The synthetic compound libraries are commercially available from Maybridge Chemical Co. (UK), Brandon Associates (USA), Microsource (USA), and Sigma-Aldrich (USA), and the natural compound libraries are commercially available from Pan Laboratories (USA) and MycoSearch (USA).

The test material may be obtained from various combinational library methods known in the art, for example, from a biological library method, a spatially addressable parallel solid phase or solution phase library method, a synthetic library method requiring deconvolution, a "one-bead one-compound" library method, and a synthetic library method using affinity chromatography selection. The synthetic methods of molecular libraries are disclosed in DeWitt et al., *Proc. Natl. Acad. Sci. U.S.A.* 90: 6909 (1993); Erb et al. *Proc. Natl. Acad. Sci. U.S.A.* 91: 11422 (1994); Zuckermann et al., *J. Med. Chem.* 37: 2678 (1994); Cho et al., *Science* 261: 1303 (1993); Carell et al., *Angew. Chem. Int. Ed. Engl.* 33: 2059 (1994); Carell et al., *Angew. Chem. Int. Ed. Engl.* 33: 2061; and Gallop et al., *J. Med. Chem.* 37: 1233 (1994).

Then, the expression level and activity of the target (e.g., semaphorin 3A) of the present invention are measured from the cells treated with the test material. The expression level and activity may be measured as described below, and as a measurement result, the test material may be determined as a material for alleviating or treating mast cell-induced inflammatory diseases if the test material increases the expression or activity of the nucleotide sequence of the marker of the present invention or inhibits the complex formation of the FcεRI receptor by the over-expressed semaphorin 3A.

According to a certain embodiment of the present invention, in step (b), the activity of semaphorin 3A is analyzed by measuring the complex formation of the FcεRI receptor by the over-expressed semaphorin 3A, and more specifically, the inhibition of the complex formation of the FcεRI receptor may be verified through the inhibition of the phosphorylation of ERK1/2, p38, and Lyn.

The screening method of the present invention may be carried out by various processes, especially by high throughput method through diverse binding assays known to those skilled in the art.

The test material or Semaphorin 3A gene or protein of the present invention may be labeled with a detectable label. For example, said detectable label includes, but not limited to, chemical label (e.g., biotin), enzyme label (e.g., horseradish peroxidase, alkaline phosphatase, peroxidase, luciferase, β-galactosidase and β-glucosidase), radioactive label (e.g., C14, 1125, P32 and S35), fluorescence label (e.g., coumarin, fluorescein, FITC (fluoresein Isothiocyanate), rhodamine 6G, rhodamine B, TAMRA (6-carboxy-tetramethyl-rhodamine), Cy-3, Cy-5, Texas Red, Alexa Fluor, DAPI (4,6-diamidino-2-phenylindole), HEX, TET, Dabsyl and FAM), luminescent label, chemiluminescent label, FRET (fluorescence resonance energy transfer) label or metal label (e.g., gold and silver).

For using the detectably labeled Semaphorin 3A gene, protein or test material, a binding of Semaphorin 3A gene or protein with test material may be analyzed through the signal generated by the label. Where using alkaline phosphatase, bromochloroindolylphosphate (BCIP), nitro blue tetrazolium (NBT), naphthol-AS-B1-phosphate and ECF (enhanced chemifluorescence) may be used as a substrate; in the case of using horseradish peroxidase, chloronaphtol, aminoethylcarbazol, diaminobenzidine, D-luciferin, lucigenin (bis-N-methylacridinium nitrate), resorufin benzyl ether, luminol, Amplex Red reagent (10-acetyl-3,7-dihydroxyphenoxazine, Pierce), HYR (p-phenylenediamine-HCL and pyrocatechol), TMB (3,3,5,5-tetramethylbenzidine), ABTS (2,2-Azine-di[3-ethylbenzthiazoline sulfonate]), OPD (o-phenylenediamine) and naphthol/pyronin may be used as a substrate.

In another aspect of this invention, the present disclosure provides a method for preventing or treating Th2-mediated immune diseases, comprising administering a composition comprising the peptide of this invention as an active ingredient to a subject.

In still another aspect of this invention, the present disclosure provides a method for preventing or treating autoimmune diseases, comprising administering a composition comprising the peptide of this invention as an active ingredient to a subject.

In still another aspect of this invention, the present disclosure provides a method for preventing or treating mast cells-induced inflammatory diseases, comprising administering a composition comprising the peptide of this invention as an active ingredient to a subject.

Since the present method uses the composition described above, the common descriptions between them are omitted in order to avoid undue redundancy leading to the complexity of this specification.

Advantageous Effects

Features and advantages of the present invention are summarized as follows.

(i) The peptide of the present invention can perform the same or similar functions to natural semaphorin 3A, and has very excellent skin penetration due to a small size thereof.

(ii) The peptide of the present invention induces mast cell-specific apoptosis, and inhibits the activity of mast cells (e.g., reducing the amount of histamine secreted, and inhibiting the activity of beta-hexosaminidase).

(iii) Furthermore, the peptide of the present invention inhibits the FcεRI signaling, more specifically, the complex formation of the FcεRI receptor, which is shown through the inhibition of the phosphorylation of ERK1/2, p38, or Lyn.

(iv) Therefore, excellent activity and stability of the peptide of the present invention can be very favorably applied to medicines, quasi-medicines, and cosmetics.

BRIEF DESCRIPTION OF THE DRAWINGS

FIG. 1 is a graph showing high-performance liquid chromatography analysis results of the peptide of SEQ ID NO: 1, prepared by the synthetic example of the present invention.

FIG. 2a illustrates flow cytometry results showing an effect of promoting apoptosis of mast cells, treated with a peptide of SEQ ID NO: 1, prepared by the synthetic example of the present invention.

FIG. 4c illustrates immunoprecipitation analysis results showing that the inhibition of IgE receptor signaling of mast cells at the time of the treatment with the peptide of SEQ ID NO: 1, prepared by the synthetic example of the present invention, is due to the suppression of the receptor complex formation.

FIG. 5 illustrates thermal stability results of the peptide of SEQ ID NO: 1, prepared by the synthetic example of the present invention.

MODE FOR CARRYING OUT THE INVENTION

Figure 2B:
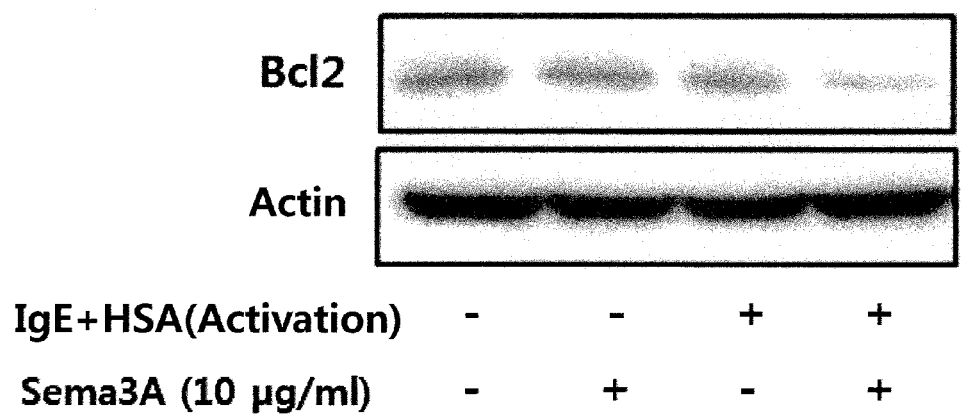
FIG. 2b illustrates Bcl2 western blotting results showing an effect of promoting apoptosis of mast cells treated with a peptide of SEQ ID NO: 1, prepared by the synthetic example of the present invention.

The present invention will now be described in further detail by examples. It would be obvious to those skilled in the art that these examples are intended to be more concretely illustrative and the scope of the present invention as set forth in the appended claims is not limited to or by the examples.

EXAMPLES

Preparation Example 1

Synthesis of Trp-Val-Pro-Tyr-Gln-Ala-Arg-Val-Pro-Tyr-Pro-Arg (SEQ ID NO:1)

700 mg of chloro trityl chloride resin (CTL resin, Nova Biochem Cat No. 01-64-0021) were introduced into a reactor, to which 10 ml of methylene chloride (MC) were added, followed by agitation for 3 min. After removing solution, 10 ml of dimethylformamide (DMF) were added to the resultant and then agitation was carried out for 3 min, after which the solvent was removed. 10 ml of dichloromethane solution were added to the reactor and 200 mmole of Fmoc-Arg(pbf)-OH (Bachem, Swiss) and 400 mmole of DIEA (N,N'-diisopropyl ethylamine) were then added to the reactor, after which the mixture was dissolved by agitation and reaction was then undertaken with agitating for 1 hr. After washing, methanol and DIEA (2:1) dissolved in DCM (dichloromethane) were reacted with the resin for 10 min, and then the resultant was washed using excess of DCM/DMF (1:1). After removing the solution, 10 ml of DMF were added to the resultant and agitation was performed for 3 min, followed by removing the solvent. 10 ml of a deprotection solution (20% piperidine/DMF) were added to the reactor and agitated for 10 min at room temperature, followed by removing the solution. After adding the same volume of the deprotection solution, the reaction was undertaken for 10 min and solution was removed, followed by washing sequentially with DMF (3 times), MC (1 times) and DMF (1 times) to yield Arg(pbf)-CTL resins. 10 ml of DMF solution was added to a new reactor and then 200 mmole of Fmoc-Pro-OH (Bachem, Swiss), 200 mmole of HoBt and 200 mmole of Bop were added, followed by agitation for solubilization. 400 mmole of DIEA was added to the reactor twice as a fraction and agitation was carried out for at least 5 min to dissolve all solid contents. The dissolved amino acids solution was introduced into the reactor containing the deprotected resin and reaction was undertaken with agitating for 1 hr at room temperature. Following the removal of the reaction solution, the resultant was agitated three times (each for 5 min) with DMF solution to remove unreacted residuals. A small amount of the reacted resin was taken to evaluate extent of reactions by Ninhydrine test. Using the deprotection solution, the deprotection was performed twice in the same manner as described above to yield Pro-Arg(pbf)-CTL resin. After washing with DMF and MC, further Ninhydrine test was carried out and the sequential attachments of amino acids below were performed as described above. Based on the amino acid sequence designed by the present inventors, Fmoc-Tyr(tBu), Fmoc-Pro, Fmoc-Val, Fmoc-Arg(pbf), Fmoc-Ala, Fmoc-Gln(Trt), Fmoc-Tyr(tBu), Fmoc-Pro, Fmoc-Val and Fmoc-Trp(Boc) were sequentially attached to resins. Fmoc-protecting group was removed by thoroughly incubating with the deprotection solution twice for 10 min. For acetylation, acetic anhydride, DIEA and HoBt were incubated with the peptidyl resins for 1 hr. The prepared peptidyl resins were washed three times with DMF, MC and methanol, respectively, and gradually dried under nitrogen atmosphere, after which it was completely vacuum-dried under $P_2O_5$. The dried resins were reacted with 30 ml of a leaving solution [containing 95% trifluroacetic acid (TFA), 2.5% distilled water, 2.5% thioanisole] for 2 hr at room temperature upon intermittent agitating. The resin was filtered and washed with a small volume of TFA solution, after which the filtrate was combined with the mother liquor. After distillation under reduced pressure to reduce the total volume by two, the precipitation was induced using 50 ml of cold ether and the formed precipitates were collected by centrifugation, followed by washing twice with cold ether. After removing the mother liquor, the resultant was completely dried under nitrogen atmosphere to yield 0.85 g of unpurified peptide 1, $NH_2$-Trp-Val-Pro-Tyr-Gln-Ala-Arg-Val-Pro-Tyr-Pro-Arg-OH (yield rate; 89.9%). The molecular weight of the final product was determined as 1531.8 (theoretical MW: 1531.795) using a mass analyzer.

TABLE 1

| SEQ ID NO | Amino acid sequence | Analyzed values (mass analyzer) | Theoretical values |
|---|---|---|---|
| 1 (Peptide-1) | WVPYQARVPYPR | 1531.8 | 1531.795 |

Test Example 1

Investigation on Mast Cell Apoptosis Effect of Activated Mast Cells Using Synthetic Peptide In order to investigate the anti-allergic effect of the peptide of SEQ ID NO: 1, prepared by synthetic example 1, the apoptosis effect of the peptide on activated mast cells was tested.

First, RBL-2H3 rat mast cell lines (Korean Cell Line Bank, Korea) were cultured in Dulbecco's modified Eagle's medium (DMEM, Gibco, U.S.A.) supplemented with 10% fetal bovine serum (FBS, Sigma) using a flask for tissue culture (SPL, Korea). The cultured cell lines were detached from the bottom of the culture container using a 1% trypsin solution, and then only cell deposits were collected by centrifugation. The cell deposits were again suspended in DMEM culture liquid, placed in each well of a 6-well plate for tissue culture (SPL, Korea) at $1 \times 10^5$ cells per well, and then cultured for 24 h under conditions of 37° C. and 5% $CO_2$. After 24 h, the medium was exchanged with the same culture liquid. In the test under activated conditions, IgE and HAS treatment was conducted, and a blank sample for determining a reference and the peptide of the present invention were dissolved in 10% distilled water in a sterile state, followed by culturing at concentrations of 1 µg/ml and 10 µg/ml for 27 h under the same conditions as above. After the completion of the culture, the culture supernatant fluid was removed, the cultured cell lines were detached from the bottom of the culture container using a 1% trypsin solution, and then only cell precipitates were collected by centrifugation. The cells were stained using an Annexin V-PI staining kit (BD pharmigen), and then FL1 and FL2 intensities were measured using flow cytometry, FACS. Annexin V-positive apoptotic cells were counted (see FIG. 2a). In order to further investigate the apoptotic effect, the cells treated under the same conditions as in the above test were obtained, and the expression level of the pro-apoptotic protein Bcl2 was confirmed by western blotting (see FIG. 2b).

Meanwhile, in order to investigate whether or not the apoptosis effect is a mast cell-specific reaction, the cytotoxicity test was conducted using HaCaT cells as keratinocytes and NIH3T3 cells as fibroblasts. The cells were placed in a 96-well plate for tissue culture at $5 \times 10^3$ cells per well, and then cultured for 24 h under conditions of 37° C. and 5% $CO_2$. After 24 h, the medium was exchanged with the same culture liquid. A blank sample for determining a reference and the synthetic peptide were dissolved in 10% distilled water in a sterile state, followed by culturing at concentrations of 1 µg/ml and 10 µg/ml for 27 h under the same conditions as above. After the completion of the culture, the culture liquid was treated with MTT reagent (5 mg/ml; SIGMA, USA) with 1/10 volume and further cultured for 4 h, and the generated formazan was dissolved in DMSO and the absorbance was measured at 540 nm using a spectrophotometer (Molecular devices, USA) (see FIG. 2c).

FIG. 2a shows FACS results of counting apoptotic mast cells after treatment with the peptide. As can be seen from FIG. 2a, it could be verified that the peptide of the present invention increased the Annexin V-positive cell count to effectively induce apoptosis in both inactivated and activated mast cells (10 µg/ml treatment group).

FIG. 2b shows western blotting results of the expression level of intracellular pro-apoptotic protein Bcl2 after treatment with the peptide. As can be seen from FIG. 2b, it could be verified that the peptide of the present invention induced apoptosis to reduce the expression level of Bcl2 in both inactivated and activated mast cells.

Figure 2C:
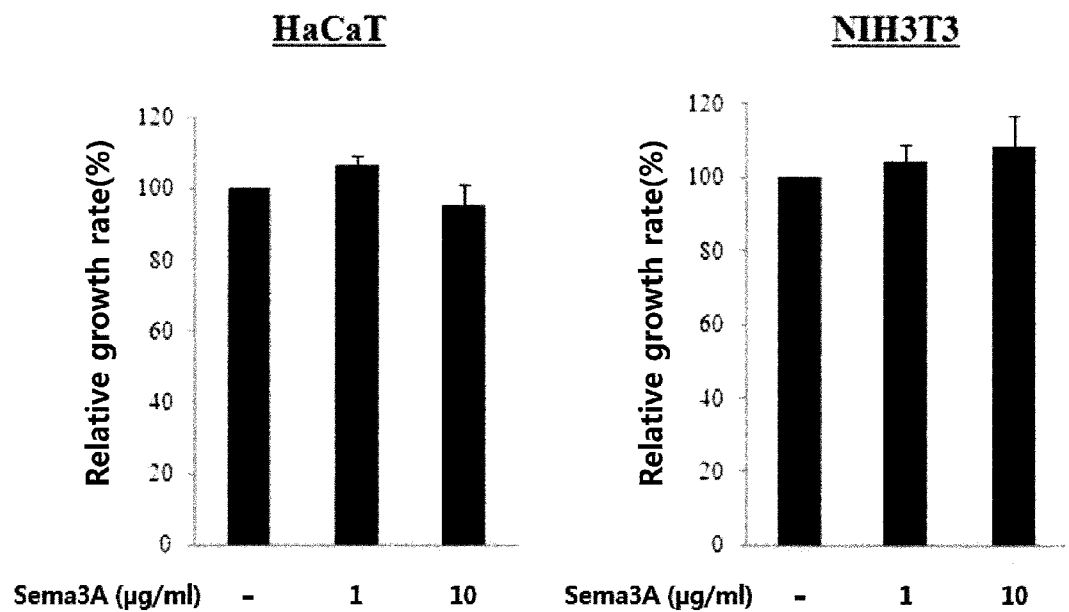
FIG. 2c illustrates cytotoxic effects on keratinocytes and fibroblasts, showing that the effect of promoting apoptosis of mast cells at the time of the treatment with the peptide of SEQ ID NO: 1, prepared by the synthetic example of the present invention, is a cell-specific reaction.

FIG. 2c shows cytotoxic results on HaCaT cells as human keratinocyte lines and NIH3T3 cells as fibroblast cell lines after treatment with the peptide. As can be seen from FIG. 2c, the peptide of the present invention did not exhibit cytotoxicity on the other skin cells excluding mast cells.

To sum the foregoing results of test example 1, it can be seen that the peptide of the present invention has activity to induce mast cell-specific apoptosis, and the activity is confirmed in both the inactivation state and the activation state through IgE (SIGMA, USA) and HSA (allergen; SIGMA, USA) treatment, but the activity is more remarkable in the activated mast cells.

Test Example 2

Investigation on Mast Cell Activity Inhibitory Efficacy of Synthetic Peptide

In the culture of RBL-2H3 cells sensitized by IgE treatment (1 μg/ml) for 16 h, the existing culture medium was removed and exchanged with a tyrode buffer. Then, the cells were treated with the peptide (1 and 10 μg/ml) synthesized in example 1 and quercetin (40 μM; SIGMA, USA) as a positive control, followed by culturing for 20 h. After that, the cells were treated with 1 μg/ml HAS as an allergen, followed by culturing for 1 h. As a result, in order to measure the amount of histamine secreted in mast cells, the cell culture liquid was collected, and a histamine ELISA kit (IBL international) was used (see FIG. 3a). In addition, in order to measure the activity of beta-hexosaminidase, the degree of color development after a reaction with a substrate, p-N-acetyl-glucosamine (NAG; SIGMA, USA) was determined by measuring the absorbance at 405 nm using a spectrophotometer (see FIG. 3b).

Figure 3A:
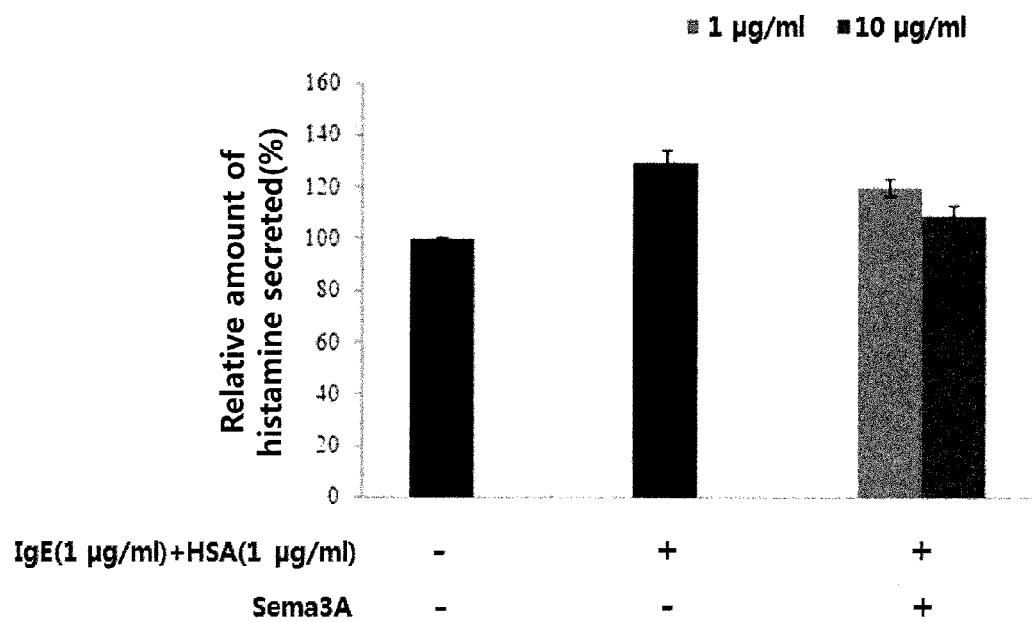
FIG. 3a illustrates ELISA results showing the reduction in the secretion of histamine from mast cells at the time of the treatment with the peptide of SEQ ID NO: 1, prepared by the synthetic example of the present invention.
Figure 3B:
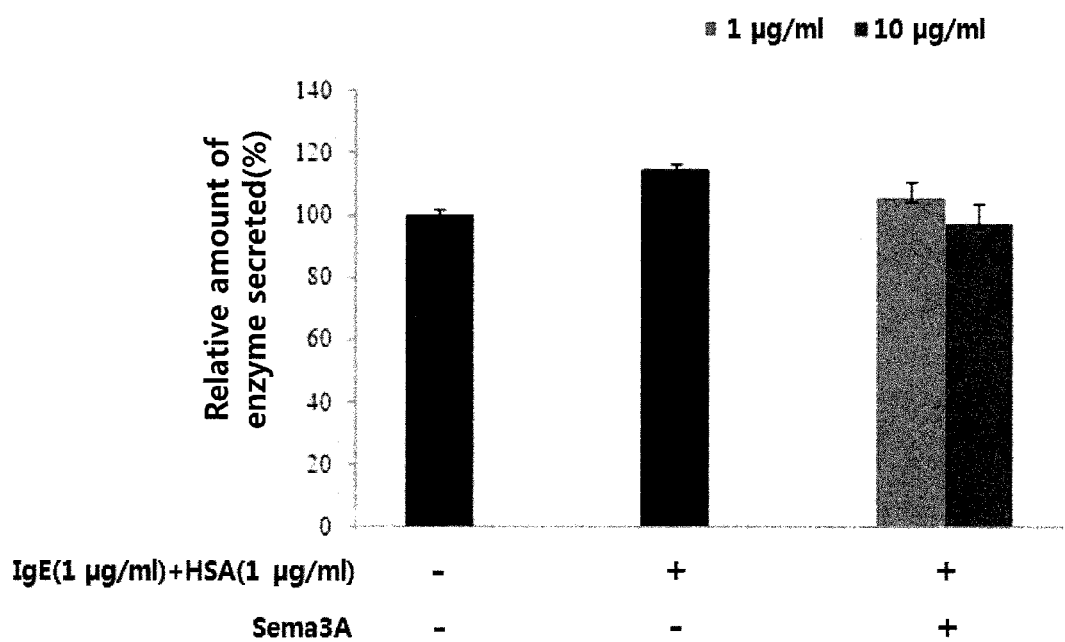
FIG. 3b illustrates activity test results showing the reduction in the secretion of beta-hexosaminidase from mast cells at the time of the treatment with the peptide of SEQ ID NO: 1, prepared by the synthetic example of the present invention.

FIG. 3a shows measurement results of the amount of histamine secreted in mast cells after treatment with the peptide. As can be seen from FIG. 3a, the activity of quercetin, as a positive control, which reduces the secretion amount of histamine, which has been increased by IgE and HSA stimulation, can be confirmed. The group treated with the peptide of the present invention also had activity to reduce the secretion amount of histamine in a concentration-dependent manner. The foregoing inhibitory activity (or tendency) could be also confirmed to be the same in the beta-hexosaminidase activity test (see FIG. 3b).

To sum the foregoing results of test example 2, the peptide of the present invention has effects of inhibiting histamine and beta-hexosaminidase secreted due to the activation of mast cells, and these effects can lead to effects of suppressing subsequent inflammation responses and itching.

Test Example 3

Verification on IgE Receptor (FcεRI) Signaling Inhibitory Effect of Synthetic Peptide In order to investigate the mast cell activity inhibitory mechanism of the peptide prepared by synthetic example 1, the effect of inhibiting the signal of FcεRI protein, as a receptor to which mast cell stimulus IgE binds, was tested. The cells were placed in a 60 mm-sized plate for culture (SPL, Korea) at $1.5 \times 10^6$ cells per well, and then cultured for 24 h under conditions of 37° C. and 5% $CO_2$. After that, the cells were treated with IgE (1 μg/ml) for 24 h for cell sensitization, and then a blank sample for determining a reference and the synthetic peptide were dissolved in 10% distilled water in a sterile state, followed by treatment with a concentration of 10 μg/ml for 20 min, and then the cells were stimulated by treatment with 1 μg/ml allergen HSA for 5 min or 30 min. The cells after the completion of all the treatments were obtained through trypsin treatment, and then the phosphorylation degree of ERK1/2, p38, and Lyn, which are molecules involved in FcεRI signaling, were confirmed by western blotting (see FIGS. 4a and 4b).

In addition, in order to investigate whether or not the FcεRI signaling inhibitory effect by the peptide of the present invention is made by the inhibition of the crosslinking of sub-chains of the IgE receptor, FcεRI, HSA stimulation was conducted for 10 min under the same test conditions, and then the cells thus obtained were subjected to immunoprecipitation using IgE antibody. After the first separation using immunoprecipitation, western blotting was conducted using FcεRI gamma sub-chain antibody to confirm the protein amount of the gamma sub-chains binding to IgE (see FIG. 4c).

Figure 4A:
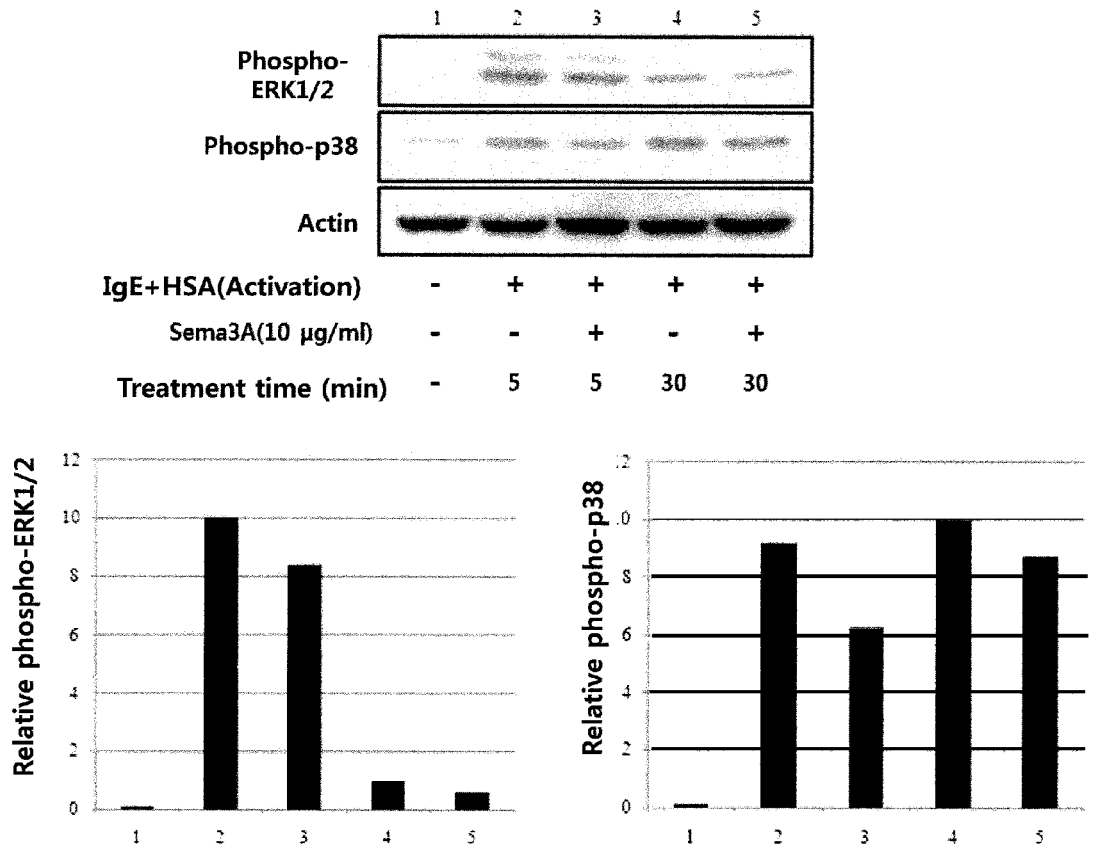
FIG. 4a illustrates graph results obtained by numerically expressing band intensities through densitometry, as test results of verifying phosphorylation levels of ERK and p38 Mark, which shows the inhibition of IgE receptor signaling of mast cells at the time of the treatment with the peptide of SEQ ID NO: 1, prepared by the synthetic example of the present invention.
Figure 4B:
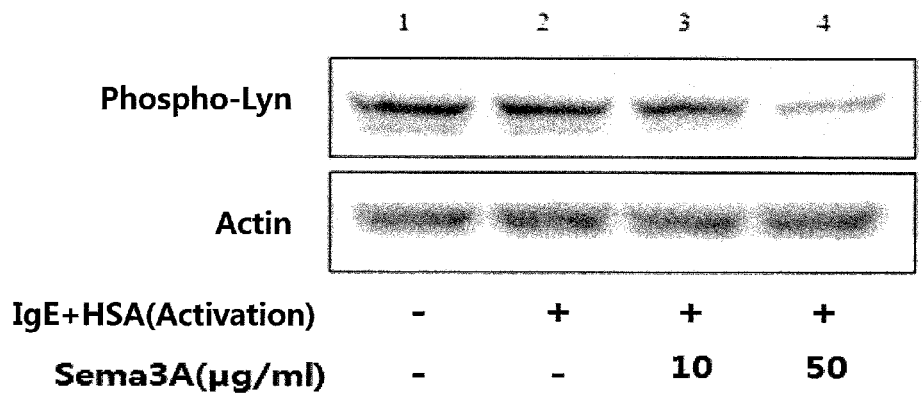
FIG. 4b illustrates test results of verifying the phosphorylation level of the receptor-related protein Lyn, which shows the inhibition of IgE receptor signaling of mast cells at the time of the treatment with the peptide of SEQ ID NO: 1, prepared by the synthetic example of the present invention.

FIG. 4a shows observation results of the phosphorylation levels of signal proteins of IgE receptor FcεRI, expressed on surfaces of mast cells after treatment with the peptide. As can be seen from FIG. 4a, the peptide of the present invention exhibited an efficacy of inhibiting the phosphorylation of FcεRI signal proteins, ERK1/2 and p38. It was also verified that, the phosphorylation of the other protein Lyn was significantly inhibited in a concentration-dependent manner in the peptide treatment group (see FIG. 4b).

FIG. 4c shows observation results of the crosslinking between sub-chains of IgE receptor (FcεRI) after treatment with the peptide. It is known that, IgE receptor has complexes composed of alpha, beta, and gamma sub-chains, and if the binding to IgE occurs by the alpha sub-chain, the beta and gamma sub-chains gather to form complexes. Thus, in order to investigate the activity of the peptide of the present invention to inhibit the complex formation of the FcεRI receptor, the immunoprecipitation using IgE antibody was conducted, and then western blotting was conducted on the gamma sub-chains. As a result, the peptide of the present invention was verified to have activity to significantly inhibit the complex formation of FcεRI receptor.

To sum the foregoing results of test example 3, the peptide of the present invention inhibits the complex formation of FcεRI receptor, which is present on surfaces of mast cells and involved in cell activity, thereby exhibiting the efficacy of blocking FcεRI signaling.

Test Example 4

Thermal Stability of Prepared Peptide

The peptide prepared by synthetic example 1 and a standard form growth factor (Semaphorin 3A) purchased from NIBSC (UK) were formed to give 0.1 mg/ml using phosphate buffered saline. 1 ml of the prepared solution was placed in each glass vial, and allowed to stand at 37° C. The solution standing at 37° C. was sampled on days 0, 5, 10, 20, 30, 50, and 70. Centrifugation for each day was conducted to remove modified peptides or proteins, and the supernatant was taken. HPLC was used for quantification (see FIG. 5).

Example 1

Preparation of Nano Peptides 50 mg of peptide synthesized in preparation Examples was dissolved in 500 ml of distilled water by sufficient agitation. The peptide solution was mixed with 5 g lecithin, 0.3 ml sodium oleate, 50 ml ethanol and a small amount of oils, and its volume was adjusted with distilled water to 1 L. The resulting solution was subjected to a microfluidizer under high pressure for emulsification, thereby providing nanosomes having about 100-nm size. The nanosomes were prepared to have a final concentration of about 50 ppm and used as ingredients for cosmetics.

Formulation Example 1

Skin Softener

A skin softener comprising peptide-containing nanosomes prepared in Example 1 was formulated according to the following composition:

TABLE 2

| Ingredients | Content (wt %) |
|---|---|
| Peptide nanosome | 0.001 |
| 1,3-butylene glycol | 6.0 |
| Glycerin | 4.0 |
| PEG 1500 | 1.0 |
| Sodium hyaluronate | 1.0 |
| Polysorbate 20 | 0.5 |
| Ethanol | 8.0 |
| Preservative, pigment | Proper amount |
| Benzophenone-9 | 0.05 |
| Perfume | Minute amount |
| Distilled water | Residual amount |
| Total | 100 |

Formulation Example 2

Moisture Cream

A moisture cream comprising peptide-containing nanosomes prepared in Example 1 was formulated according to the following composition:

TABLE 3

| Ingredients | Content (wt %) |
|---|---|
| Peptide nanosome | 0.001 |
| Meadowfoam oil | 3.0 |
| Cetearylalcohol | 1.5 |
| Stearic acid | 1.5 |
| Glyceryl stearate | 1.5 |
| Liquid paraffin | 10.0 |
| Wax | 2.0 |
| Polysorbate 60 | 0.6 |
| Sorbitan sesquiolate | 2.5 |
| Squalane | 3.0 |
| 1,3-butylene glycol | 3.0 |
| Glycerin | 5.0 |
| Triethanol amine | 0.5 |
| Tocopheryl acetate | 0.5 |
| Preservative, pigments | Proper amount |
| Perfume | Proper amount |
| Distilled water | Residual amount |
| Total | 100 |

Formulation Example 3

Moisture Liquid

A moisture liquid comprising peptide-containing nanosomes prepared in Example 1 was formulated according to the following composition:

TABLE 4

| Ingredients | Content (wt %) |
|---|---|
| Peptide nanosome | 0.002 |
| 1,3-butylene glycol | 4.0 |
| Glycerin | 4.0 |
| Cetearyl alcohol | 0.8 |
| Glyceryl stearate | 1.0 |
| Triethanol amine | 0.13 |
| Tocopheryl acetate | 0.3 |
| Liquid paraffin | 5.0 |
| Squalane | 3.0 |
| Makadamianut oil | 2.0 |
| Polysorbate 60 | 1.5 |
| Sorbitan sesquiolate | 0.5 |
| Carboxyvinyl polymer | 1.0 |
| Preservative, pigments | Proper amount |
| Perfume | Proper amount |
| Distilled water | Residual amount |
| Total | 100 |

Formulation Example 4

Essence

An essence comprising peptide-containing nanosomes prepared in Example 1 was formulated according to the following composition:

TABLE 5

| Ingredients | Content (wt %) |
|---|---|
| Peptide nanosome | 0.005 |
| Glycerin | 10.0 |
| 1,3-butylene glycol | 5.0 |
| PEG 1500 | 2.0 |
| Allantoin | 0.1 |
| DL-panthenol | 0.3 |
| EDTA-2Na | 0.02 |
| Hydroxyethyl cellulose | 0.1 |
| Sodium hyaluronate | 8.0 |
| Carboxyvinyl polymer | 0.2 |
| Triethanol amine | 0.18 |
| Octyldodeceth-16 | 0.4 |
| Ethanol | 6.0 |
| Perfume, preservative, pigments | Proper amount |
| Distilled water | Residual amount |
| Total | 100 |

Having described a preferred embodiment of the present invention, it is to be understood that variants and modifications thereof falling within the spirit of the invention may become apparent to those skilled in this art, and the scope of this invention is to be determined by appended claims and their equivalents.

The invention claimed is:

1. A peptide consisting of the amino acid sequence of SEQ ID NO: 1.

2. The peptide of claim 1, wherein the peptide is derived from human semaphorin 3A (Sema3A) protein.

3. The peptide of claim 1, wherein the peptide induces mast cell-specific apoptosis.

4. The peptide of claim 1, wherein the peptide has activity to reduce the amount of histamine secreted by mast cells.

5. The peptide of claim 1, wherein the peptide inhibits intracellular activity of beta-hexosaminidase.

6. The peptide of claim 1, wherein the peptide induces the inhibition of Fc epsilon Receptor I alpha (FcεRI) signaling.

7. The peptide of claim 6, wherein the inhibition of FcεRI signaling is implemented through the suppression of the complex formation of FcεRI receptor.

8. The peptide of claim 6, wherein the inhibition of FcεRI signaling inhibits the phosphorylation of Extracellular-Signal Regulated Kinase 1/2 (ERK1/2), p38, or Lck/Yes Novel Tyrosine Kinase (Lyn).

9. The peptide of claim 1, wherein the N- or C-terminal of the peptide further comprises a protective group selected from the group consisting of an acetyl group, a fluorenyl methoxy carbonyl group, a formyl group, a palmitoyl group, a myristyl group, a stearyl group, and polyethylene glycol (PEG).

10. A method for treating a Th-mediated immune disease, the method comprising administering to a subject the composition containing, as an active ingredient, the peptide of claim 1.

11. The method of claim 10, wherein the Th2-mediated immune disease is allergic rhinitis, bronchial asthma, atopic dermatitis, contact dermatitis, allergic conjunctivitis, urticaria, vascular edema, food allergy, physical allergy, hypersensitive pneumonitis, occupational allergic diseases, or drug allergy.

12. A method for treating an autoimmune disease, the method comprising administering to a subject the composition containing, as an active ingredient, the peptide of claim 1, wherein the autoimmune disease is selected from the group consisting of obesity, hyperlipidemia, diabetes, atherosclerosis, and metabolic syndrome.

13. A method for treating a mast cell-induced inflammatory disease, the method comprising administering to a subject the composition containing, as an active ingredient, the peptide of claim 1, wherein the mast cell-induced inflammatory disease is selected from the group consisting of asthma, atopic dermatitis, psoriasis, interstitial cystitis, obesity, multiple sclerosis, coronary artery disease (CAD), arthritis, and inflammatory bowel disease (IBD).

14. The method of claim 13, wherein the composition induces mast cell-specific apoptosis.

* * * * *